(12) United States Patent
Janik et al.

(10) Patent No.: US 7,110,113 B1
(45) Date of Patent: Sep. 19, 2006

(54) FILM MEASUREMENT WITH INTERLEAVED LASER CLEANING

(75) Inventors: Gary R. Janik, Palo Alto, CA (US); Dan G. Georgesco, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 364 days.

(21) Appl. No.: 10/616,064

(22) Filed: Jul. 8, 2003

Related U.S. Application Data

(60) Provisional application No. 60/426,138, filed on Nov. 13, 2002.

(51) Int. Cl.
*G01J 4/00* (2006.01)
*B08B 7/00* (2006.01)

(52) U.S. Cl. ............... 356/369; 134/1; 134/1.3

(58) Field of Classification Search ............... 356/369, 356/364, 432; 134/1, 1.3
See application file for complete search history.

(56) References Cited

U.S. PATENT DOCUMENTS

| | | | | |
|---|---|---|---|---|
| 5,261,965 A | * | 11/1993 | Moslehi | ............... 134/1 |
| 5,814,156 A | * | 9/1998 | Elliott et al. | ............... 134/1 |
| 6,704,101 B1 | * | 3/2004 | Rangarajan et al. | ..... 356/237.2 |
| 6,930,771 B1 | * | 8/2005 | Rosencwaig et al. | .... 356/237.1 |

* cited by examiner

*Primary Examiner*—Gregory J. Toatley, Jr.
*Assistant Examiner*—Roy M. Punnoose
(74) *Attorney, Agent, or Firm*—Bever, Hoffman & Harms, LLP; Jeanette S. Harms

(57) ABSTRACT

A system for analyzing a thin film simultaneously applies a pulsed cleaning beam and a measurement beam to an analysis location on a test sample to enhance measurement accuracy. The pulsed cleaning beam prevents contaminant regrowth on the analysis location during the actual measurement. To minimize the effects of thermal transients from the pulsed cleaning beam on measurement data, cleaning pulses can be timed to fall between data samples. Alternatively, data sampling can be blocked during each cleaning operation (i.e., each cleaning pulse and subsequent cooldown period) or data levels can be clamped at measurement levels from just before the start of the cleaning operation for the duration of the cleaning operation. Alternatively, data samples taken during each cleaning operation can be discarded or replaced with data samples from just before the cleaning operation using post-processing techniques.

40 Claims, 9 Drawing Sheets

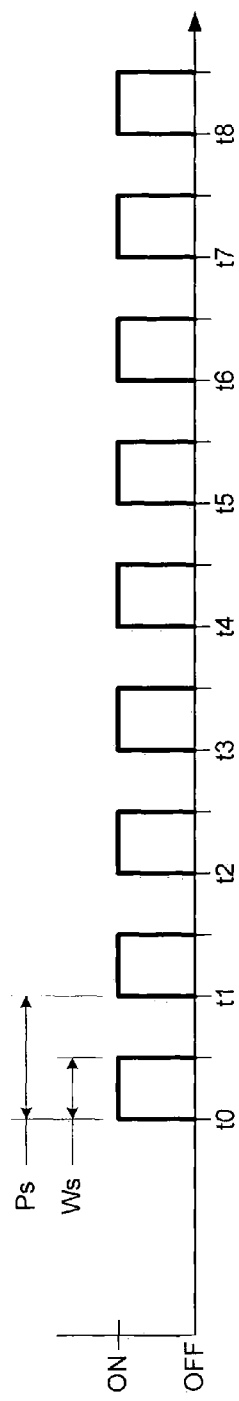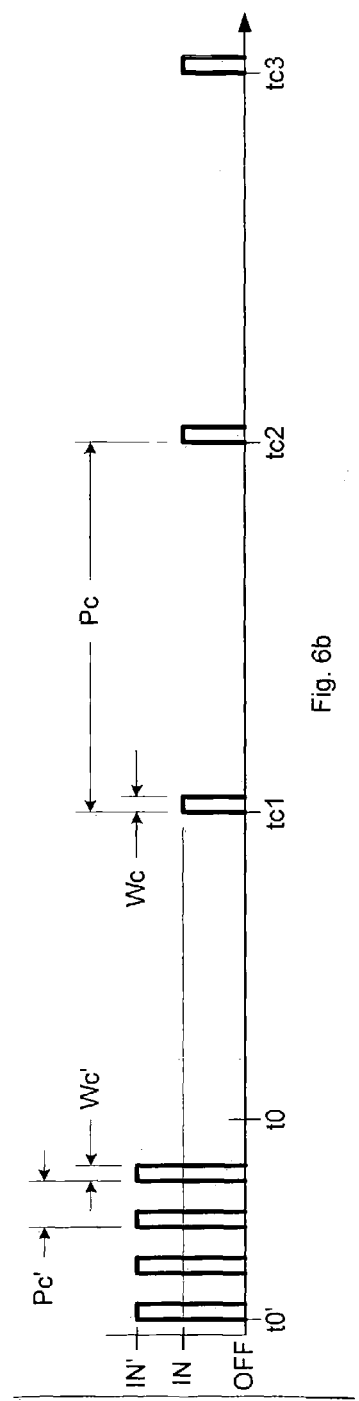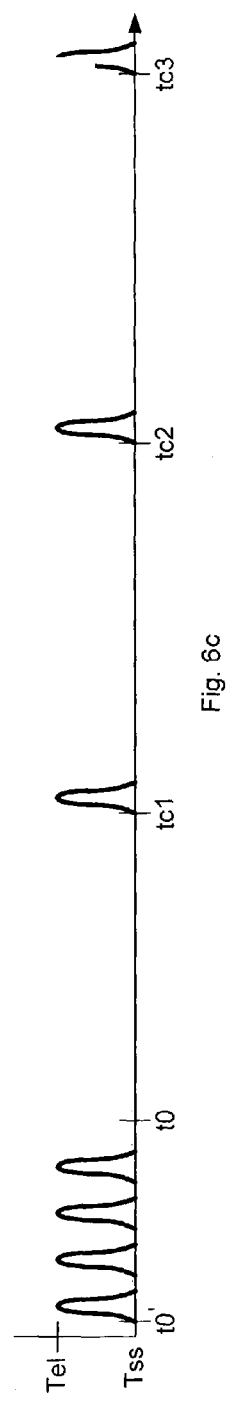

FILM MEASUREMENT WITH INTERLEAVED LASER CLEANING

CLAIM OF PRIORITY

This application claims priority to U.S. provisional application Ser. No. 60/426,138, filed Nov. 13, 2002 entitled "Film Measurement With Interleaved Laser Cleaning".

FIELD OF THE INVENTION

This invention relates generally to measurement systems, and more particularly to a system and method for minimizing contamination effects on metrology operations.

BACKGROUND OF THE INVENTION

As the dimensions of semiconductor devices continue to shrink, accurate and efficient characterization of the components forming those devices becomes more critical. Typically, the manufacturing process for modern semiconductor devices includes the formation of a number of layers or "thin films" on a silicon wafer. The thin films can include oxide, nitride, and/or metal layers, among others. To ensure proper performance of the finished semiconductor devices, the thickness and composition of each thin film formed during the manufacturing process must be tightly controlled.

Modern thin films have reached the point where the accuracy and reproducibility of thin film metrology (i.e., measurement and/or inspection) can be limited by contamination on the surface of the thin film. For example, airborne molecular contamination (AMC) such as water and other vapors can be absorbed onto the thin film, creating a contaminant layer that adversely affects thin film analysis techniques such as optical ellipsometry, optical reflectometry, grazing-incidence x-ray reflectometry (GXR), x-ray fluorescence (XRF), electron microprobe analysis (EMP), and non-contact electrical analysis—all of which operate by directing a probe beam (optical, x-ray, electron or corona discharge) at the surface of the thin film to be measured. The contaminant layer can also interfere with measurements techniques that physically contact the surface of the thin film, such as contact-based electrical analysis (e.g., spreading resistance analysis).

Conventional methods for cleaning thin films include heating the entire wafer in an oven to a temperature of about 300° C. to vaporize any contaminant layer. FIG. 1a shows a conventional oven-based wafer cleaning system 100a used to prepare a wafer 110 for thin film analysis, as described in U.S. Pat. No. 6,325,078, issued Dec. 4, 2001 to Kamieniecki. Wafer 110 includes a thin film layer 112 formed on a silicon substrate 111, and a contaminant layer 113 formed on the surface of thin film layer 112. Wafer cleaning system 100a comprises a wafer stage 120, and multiple heat lamps 130. Wafer stage 120 positions wafer 110 under heat lamps 130, where thermal radiation from heat lamps 130 heats wafer 110 to vaporize contaminant layer 113. It is believed that this cleaning process is aided by optical photons from heat lamps 130 breaking bonds between contaminant layer 113 and thin film layer 112.

FIG. 1b shows another conventional wafer cleaning system 100b used to prepare wafer 110 for thin film analysis, as described in U.S. Pat. No. 6,261,853, issued Jul. 17, 2001 to Howell et al. Just as described with respect to FIG. 1a, wafer 110 includes a thin film layer 112 formed on a silicon substrate 111 and a contaminant layer 113 formed on the surface of thin film layer 112. Cleaning system 100b incorporates a stage 140 that includes a heating element 141. Heat generated by heating element 141 is conducted through stage 140 into wafer 110, thereby providing the heating required to vaporize contaminant layer 113. A heat exchanger can be coupled to stage 140 to capture excess heat from heating element 141 to minimize undesirable heating of cleaning system 100b itself and the surrounding environment.

Although wafer cleaning systems 100a and 100b use different thermal energy sources (i.e., heat lamps 130 and heating element 141, respectively), both systems perform a bulk heating operation to remove contaminant layer 113. The large thermal control components (e.g., lamps, heated stages, heat exchangers, etc.) typically used for bulk wafer heating undesirably increase the cleanroom space required for these conventional cleaning systems. Further exacerbating the problem of excess equipment size, conventional cleaning systems are sometimes stand-alone units used in conjunction with a thin film analysis tool. Therefore, conventional cleaning systems can significantly increase the total footprint required for a complete thin film analysis system. The use of a separate cleaning system also has an adverse effect on throughput, as time must be spent transferring the wafer to and from the cleaning system. In addition, contaminants can redeposit on the cleaned wafer while it is being transferred from the cleaning-system to the film analysis tool.

In an attempt to somewhat alleviate these equipment size and recontamination problems, attempts have been made to combine wafer cleaning and measurement capabilities in a single tool. For example, the aforementioned U.S. Pat. No. 6,261,853 describes integrating cleaning system 100b with an existing metrology tool (Opti-Probe 5240 from Therma-Wave, Inc.). Also, the Quantox XP tool from KLA-Tencor integrates a wafer cleaning system similar to cleaning system 100b with a non-contact electrical film measurement system. However, any bulk wafer heating system must still incorporate the aforementioned (large) thermal control components. Furthermore, even if a combined system is used, the bulk heating operation can significantly degrade overall wafer processing throughput. Several seconds are required to heat the wafer to the temperature required for removal of the contaminant layer, and another several seconds are required to cool down the wafer after cleaning. Any wafer handling operations that must be performed during and after the cleaning operation (e.g., transferring the wafer from the cleaning system to the thin film analysis system) further reduces the throughput. Note also that any delays after cleaning allow contaminant regrowth on the wafer.

To improve throughput and reduce system footprint, a laser cleaning system can be incorporated into a metrology system. FIG. 2a shows an integrated laser cleaning metrology system 200, which is described in detail in co-owned and co-pending U.S. patent application Ser. No. 10/056,271. Metrology system 200 comprises a stage 220, an energy beam source 230, and an analysis module 240. The compact components used in an energy-beam based cleaning system (such as energy beam source 230) can be efficiently integrated into metrology system 200 to minimize system footprint.

Stage 220 holds a test sample 210 that comprises a thin film layer 212 formed on a substrate 211 and a contaminant layer 213 formed on the surface of thin film layer 212. Energy beam source 230 directs an energy beam 231 at a spot 214a on contaminant layer 213 to expose the underlying portion of thin film layer 212. Then in FIG. 2b, stage 220 positions test sample 210 under analysis module 240 so that a measurement beam 246 can be directed onto thin film layer 212 through an opening 214b formed by the laser heating of spot 214a during the preceding cleaning operation (as shown in FIG. 2a). Since only a localized portion of contaminant layer 213 is cleaned, the long heating and cooling times associated with conventional cleaning systems can be avoided to improve throughput, and the only delay between cleaning and measurement is the time required to reposition test sample 210 under analysis subsystem 240—typically 1–2 seconds.

However, as metrology parameters become ever more sensitive to AMC, even this 1–2 second delay between cleaning and measurement can allow an excessive amount of AMC recontamination onto the thin film layer. For example, many modern metrology operations require test sample surface stabilities on the order of a tenth of an angstrom. However, AMC regrowth rates can be in the 1 Å/sec range, in which case a repositioning delay of even a second can lead to significant measurement inaccuracies. Furthermore, since the measurement process itself can take a few seconds to complete, significant AMC regrowth can actually take place over the course of the measurement operation.

Accordingly, it is desirable to provide a method and system for performing thin film metrology that avoids the aforementioned problems associated with AMC contamination and regrowth.

SUMMARY OF THE INVENTION

The present invention provides a system and method for concurrent localized cleaning and analysis of a test sample to provide enhanced measurement accuracy. By performing a localized cleaning operation(s) during the actual analysis operation (i.e., "interleaving" cleaning and analysis operations), analysis degradation due to contaminant layer regrowth can be minimized. Furthermore, by eliminating the need for repositioning of the test sample between cleaning and analysis operations, throughput is enhanced while the potential for misalignment (due to the repositioning operation) is reduced.

A metrology system in accordance with an embodiment of the present invention comprises a cleaning subsystem, an analysis subsystem, a focusing subsystem, and a stage. The stage holds a test sample (such as a wafer) to be analyzed by the analysis subsystem. The analysis subsystem can comprise any metrology system or systems, including an ellipsometry system, such as a single-wavelength ellipsometry system (SWE) or a spectroscopic ellipsometry system (SE), a reflectometry system, a contact-based electrical measurement system, a non-contact electrical measurement system, a GXR system, an XRF system, an EMP system, and/or a scanning electron microscope (SEM) inspection or review system. More generally, the cleaning subsystem can be integrated with any sort of measurement system, such as metrology systems used in the production of semiconductor devices.

The focusing subsystem positions the analysis subsystem and the cleaning subsystem relative to the stage such that a measurement beam (or probe) from the analysis subsystem and a pulsed cleaning beam generated by the cleaning subsystem are simultaneously focused on the test sample. According to an embodiment of the invention, the analysis subsystem includes a measurement emitter for generating and directing the measurement beam at a analysis location, and also includes a measurement receiver for measuring the output beam(s) generated from (i.e., reflected by, emitted from, scattered by, etc.) the analysis location in response to the measurement beam so that the test sample can be analyzed. The cleaning subsystem includes a cleaning beam emitter for generating and directing the cleaning beam at the same analysis location. By performing a cleaning operation during the analysis operation, the cleaning system minimizes contaminant regrowth and provides a stable analysis environment for the analysis subsystem.

According to an embodiment of the invention, the cleaning beam can comprise a series of cleaning pulses, i.e., a series of on/off states. This in turn helps to minimize any effect the cleaning operation might have on the measurement operation. Depending on the characteristics of the pulsed cleaning beam, the pulse (on) portions may introduce local effects that could affect the measurements being taken by the analysis subsystem (of course, the non-pulse (off) portions of the pulsed cleaning beam will have no effect on the measurements). For example, each pulse of a laser cleaning beam could cause localized heating of the test sample that could in turn affect measurements taken at this elevated temperature.

Depending on the specific cleaning effects and the sensitivity of the analysis subsystem to those effects, various approaches can be taken to minimize their impact. According to an embodiment of the invention, if the cleaning effects are small enough, they can simply be ignored. According to another embodiment of the invention, the width (i.e., the duration of the pulse) and period (i.e., the time between the start of one pulse and the next) of the cleaning pulses in the pulsed cleaning beam could be timed to fall between measurement samples taken by the measurement subsystem. According to another embodiment of the invention, the analysis subsystem can include a clamp circuit that clamps measurement samples taken during each cleaning pulse (and during the cooldown period after each cleaning pulse) at the level of a measurement sample just before the cleaning pulse. According to another embodiment of the invention, post-processing can be performed on the sampled data to delete or replace measurement samples taken during each cleaning pulse and associated cooling period.

The present invention will be more fully understood in view of the following description and drawings.

BRIEF DESCRIPTION OF THE DRAWINGS

These and other features, aspects and advantages of the present invention will become better understood with regard to the following description, appended claims, and accompanying drawings.

FIGS. 6a, 6b, and 6c are graphs comparing sampling rate with cleaning pulses and cleaning effects according to an embodiment of the invention.

DETAILED DESCRIPTION

Figure 1A:
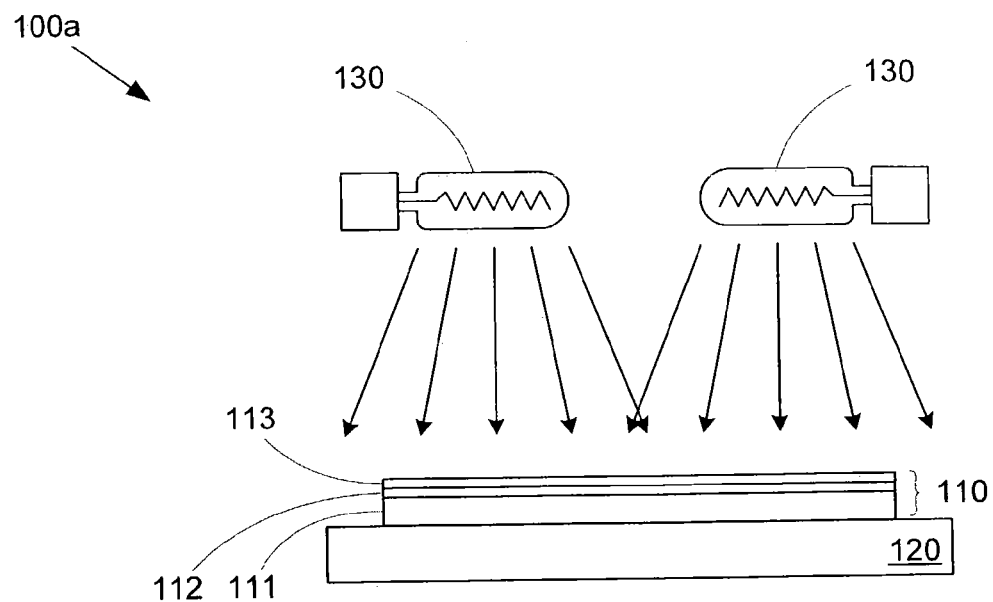
FIGS. 1a and 1b are schematic diagrams of conventional wafer cleaning systems.
Figure 1B:
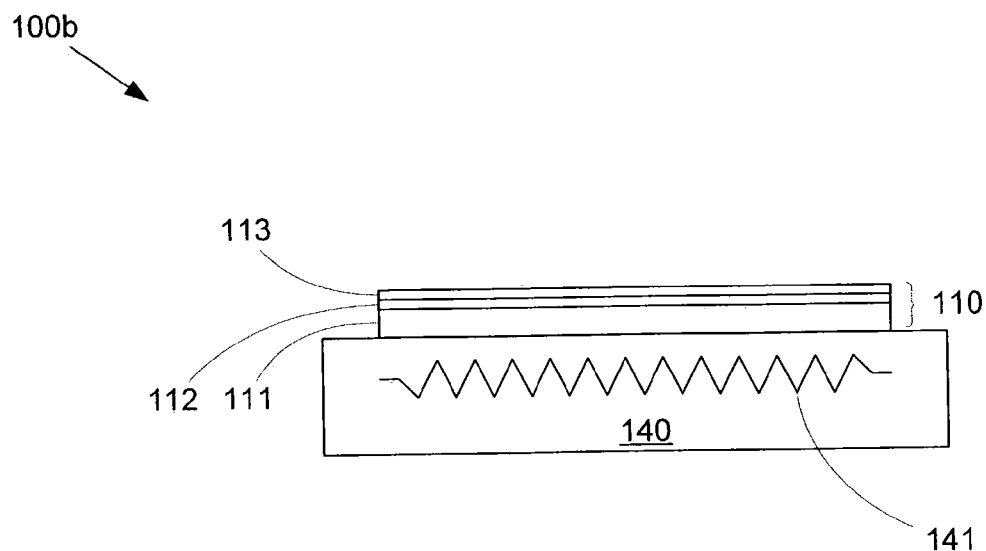
Figure 2A:
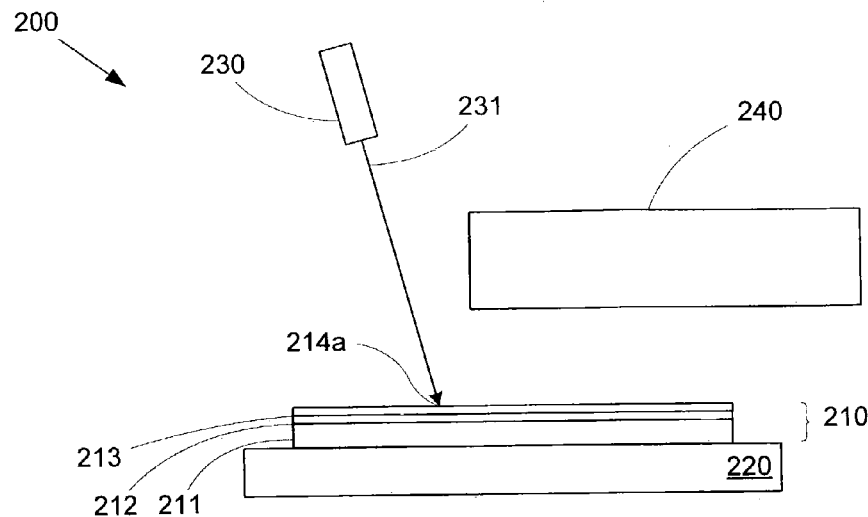
FIGS. 2a and 2b are schematic diagrams of another wafer cleaning system.
Figure 2B:
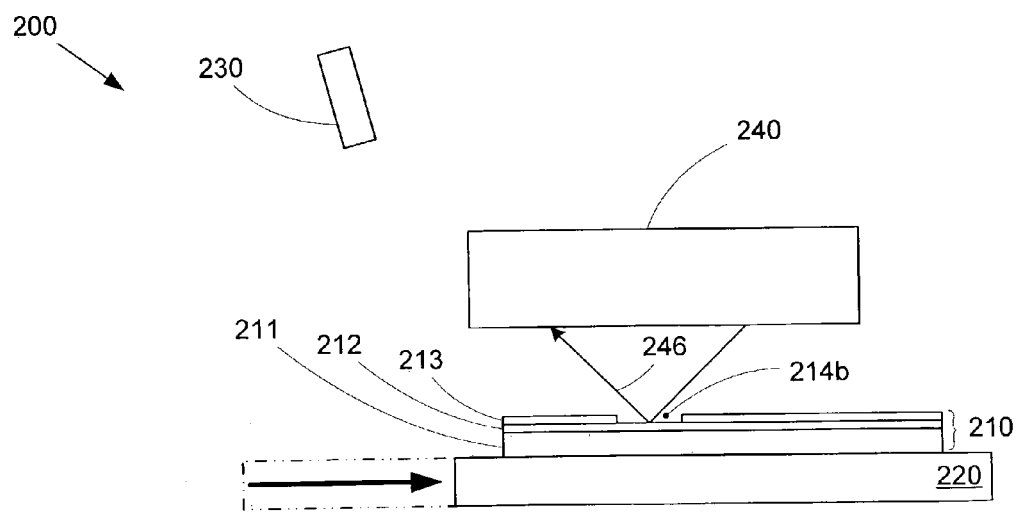
Figure 3A:
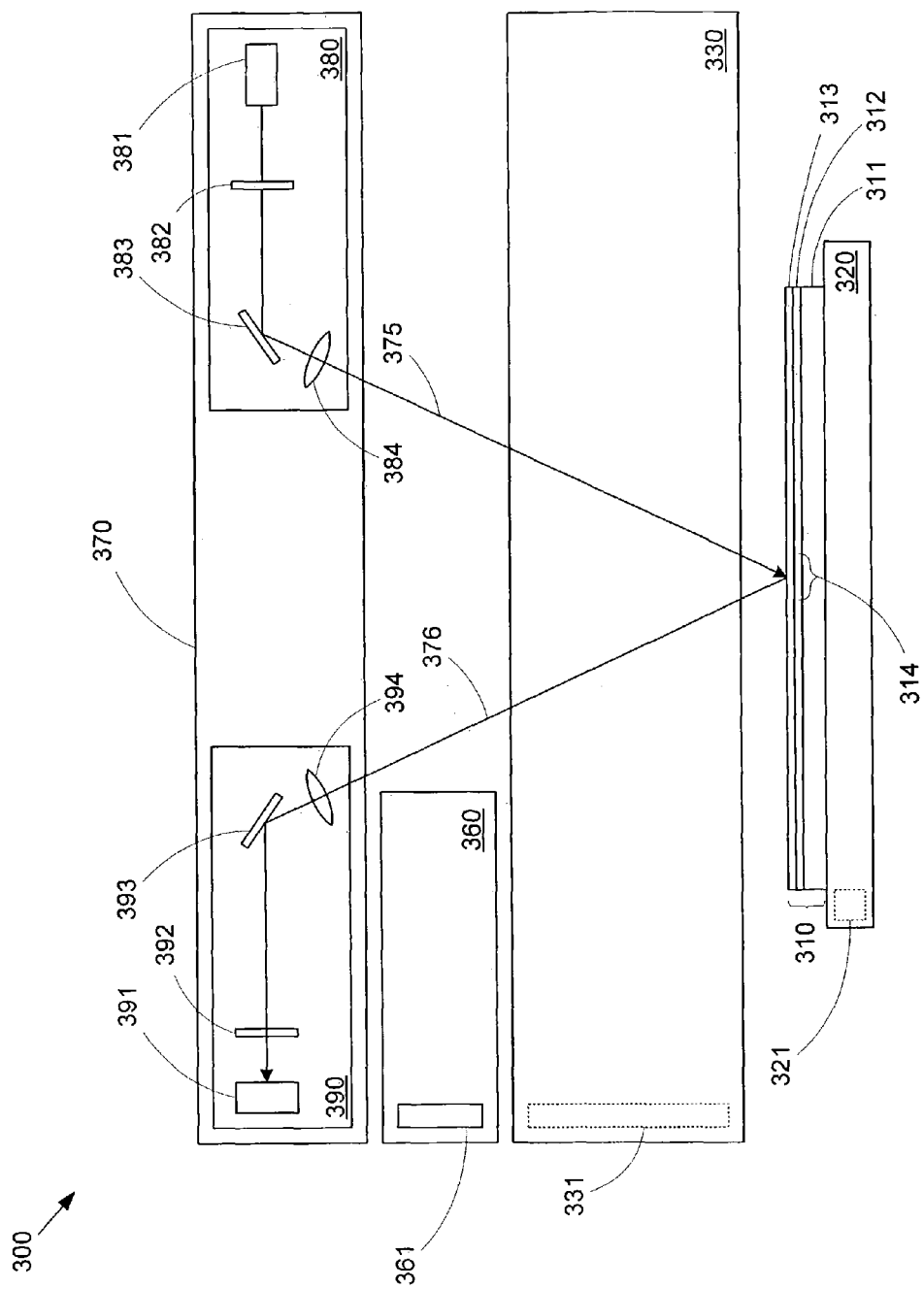
FIGS. 3a, 3b, 3c and 3d are schematic diagrams of a metrology system including interleaved cleaning capability in accordance with an embodiment of the invention.

FIG. 3a shows a metrology system 300 that includes interleaved cleaning capability in accordance with an embodiment of the invention. Metrology system 300 includes a stage 320, an analysis subsystem 330, a cleaning subsystem 360, and a focusing subsystem 370. Stage 320 holds a test sample 310 that comprises a thin film layer 312 formed on a substrate 311. Substrate 311 can comprise any structure on which thin film layer 312 can be formed, including a single-layer structure (such as a silicon wafer) or a multi-layer structure (such as an additional thin film layer or layers formed on a silicon wafer). Test sample 310 also includes a contaminant layer 313 formed on the surface of thin film layer 312. Contaminant layer 313 can comprise any unwanted material, such as AMC, on the surface of thin film layer 312. Note that while contaminant layer 313 is shown covering the entire surface of thin film layer 312 for explanatory purposes, contaminant layer 313 can also only partially cover thin film layer 312.

To perform a metrology operation, an alignment operation is first performed using focusing subsystem 370 to properly align analysis subsystem 330 and cleaning subsystem 360 with test sample 310. According to an embodiment of the invention, focusing subsystem 370 includes a focusing emitter 380 and a focusing receiver 390. For explanatory purposes, focusing emitter 380 is shown comprising an alignment beam source 381, a protective filter 382, directional optics 383, and a lens 384, while focusing receiver 390 is shown comprising a position-sensitive detector 391, a protective filter 392, directional optics 393, and a lens 394. However, focusing emitter 380 and focusing receiver 390 can comprise any components that are capable of providing the desired focusing performance.

To perform a focusing operation, alignment beam source 381 generates an alignment beam 375. According to an embodiment of the invention, alignment beam source 381 can comprise various light sources, including white-light lamps, such as xenon discharge lamps or tungsten halogen lamps, light-emitting diodes (LEDs), or near-infrared (NIR) lasers. Alignment beam 375 passes through protective filter 382 and is guided by directional optics 383 through a lens 384 that focuses alignment beam 375 onto an analysis location 314. Alignment beam 375 penetrates contaminant layer 313, which is very thin and therefore has a negligible effect on the focusing operation. A resulting reflected alignment-beam 376 is then focused by lens 394 and directed by directional optics 393 through protective filter 392 onto position sensitive detector 391. Position sensitive detector 391 measures the positional characteristics of reflected alignment beam 376, from which an accurate position for test sample 310 can be trigonometrically determined. Protective filters 382 and 392 prevent stray light (e.g., ambient light, measurement or cleaning light, etc.) from damaging or interfering with the measurements of focusing subsystem 370. For example, if alignment beam source 381 is a white-light lamp or a NIR laser, protective filters 382 and 392 can comprise NIR filters (i.e., filters that only pass NIR-light).

Once the position of test sample 310 is known, the position of analysis-subsystem 330 can be adjusted relative to stage 320 via an optional adjustment mechanism 331 in analysis subsystem 330 and/or an optional adjustment mechanism 321 in stage 320. This positioning operation ensures that a measurement beam generated by analysis subsystem 330 (discussed below with respect to FIG. 3d) is properly focused on test sample 310. An adjustment mechanism 361 in cleaning subsystem 360 is likewise used to position cleaning subsystem 360 relative to stage 320 to ensure that a cleaning beam generated by cleaning subsystem 360 (discussed below with respect to FIG. 3b) is properly focused on test sample 310.

Figure 3B:
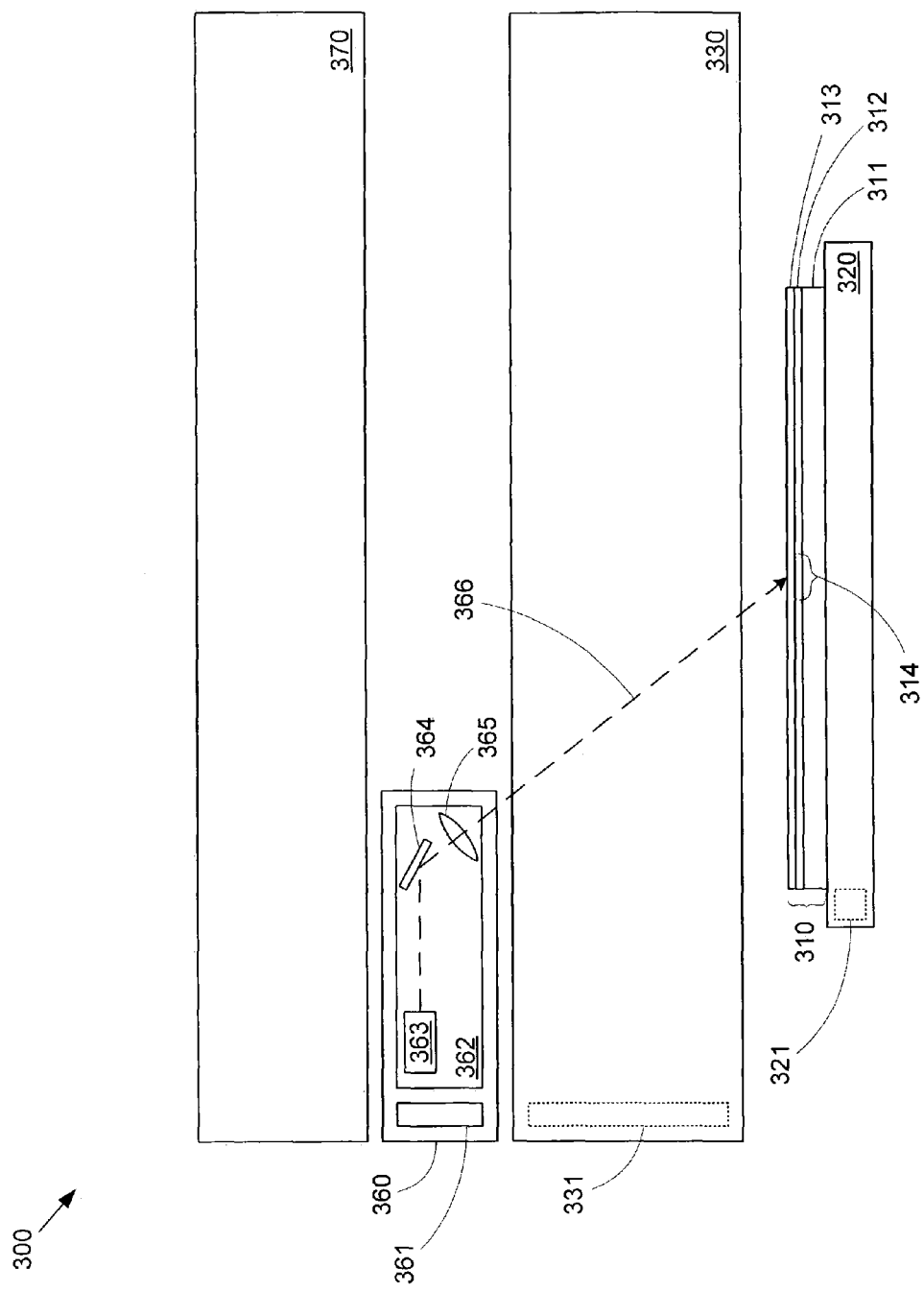

Once the alignment operation is completed, an initial cleaning operation can be performed by cleaning subsystem 360 to place analysis location 314 in the desired condition for metrology by cleaning away the overlying portion of contaminant layer 313. As shown in FIG. 3b, according to an embodiment of the invention, cleaning subsystem 360 includes a cleaning beam emitter 362 that directs a cleaning beam 366 at analysis location 314 on test sample 310. For explanatory purposes, cleaning beam emitter 362 includes a cleaning beam source 363, directional optics 364, and a lens 365. However, cleaning beam emitter can comprise any components capable of providing the desired cleaning functionality.

Cleaning beam source 363 generates cleaning beam 366, which is then guided by directional optics 364 through lens 365, which focuses cleaning beam 366 onto analysis location 314. Cleaning beam 366 is configured to remove enough of contaminant layer 313 to reveal analysis location 314 of thin film layer 312. This removal process can comprise either an interaction with contaminant layer 313 and/or an interaction with the underlying portion(s) of thin film layer 312 and/or substrate 311. For example, cleaning beam 366 could comprise a laser tuned to heat contaminant layer 313 directly or heat the underlying portion of thin film layer 312 or substrate 311. Note that the specific contaminant layer removal mechanism will depend on the type of cleaning beam used.

Figure 3C:
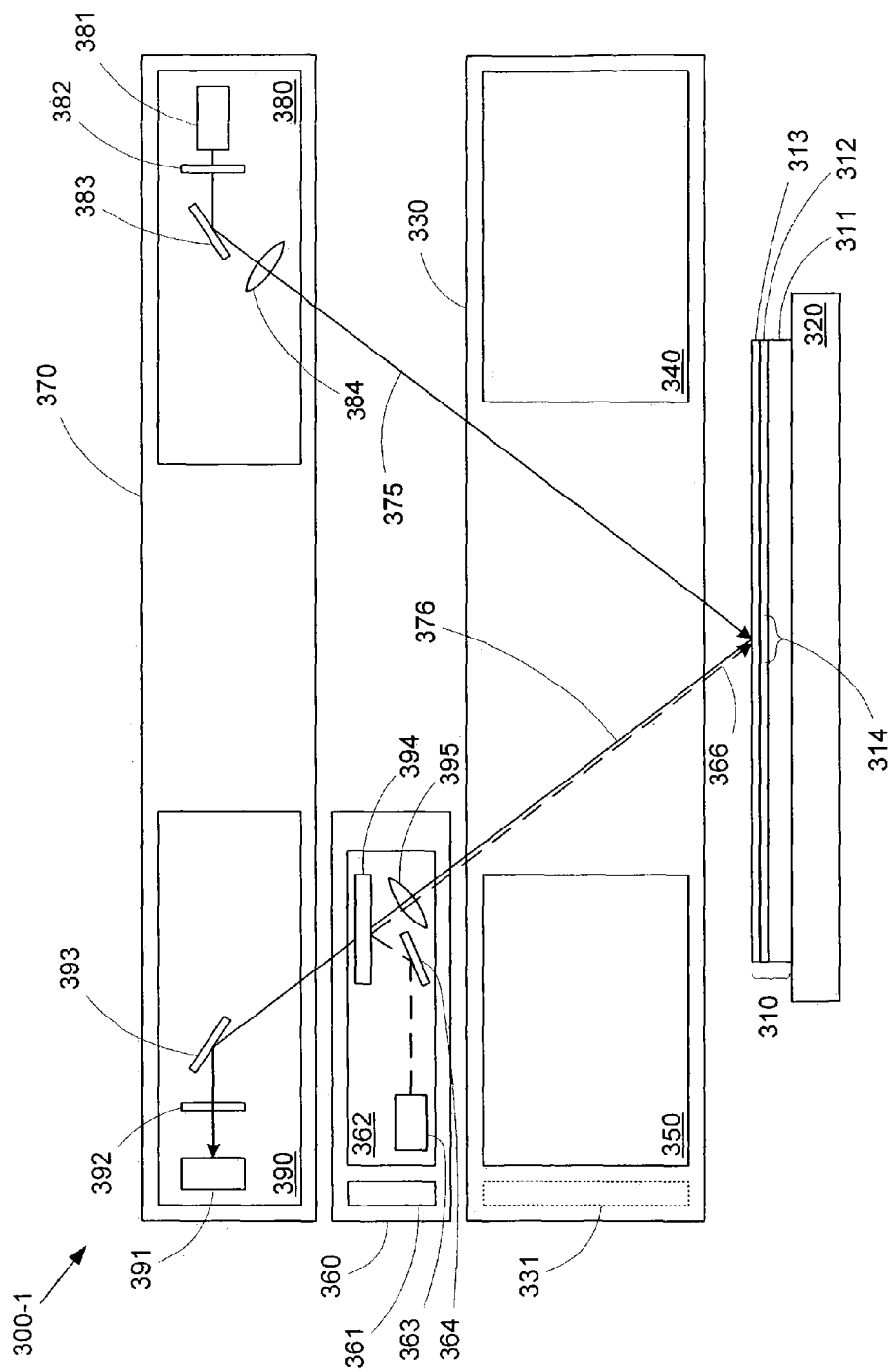

Cleaning subsystem 360 and focusing subsystem 370 can share a common optical path to optimize layout efficiency and permit the sharing of focusing optics to reduce system cost. FIG. 3c shows a metrology system 300-1 that includes interleaved cleaning capabilities in accordance with another embodiment of the invention. Metrology system 300-1 is substantially similar to metrology system 300 shown in FIGS. 3a and 3b, except that focusing receiver 390 and cleaning beam emitter 362 share a common lens 395 for focusing reflected alignment beam 376 onto position sensitive detector 391 and for focusing cleaning beam 366 onto analysis location 314, respectively. Because they use lens 395, reflected alignment beam 376 and cleaning beam 366 share a common optical path (i.e., are aligned) between lens 395 and analysis location 314 of test sample 310. A dichroic mirror 394 reflects cleaning beam 366 and transmits reflected alignment beam 376, thereby placing the two beams in alignment. As noted above, position sensitive detector 391 and alignment beam source 381 are protected from scattered cleaning light by protective filters 392 and 382, respectively.

During cleaning operations, the potential for damage to the underlying thin film layer 312 and/or substrate 311 during the cleaning process is minimal because of the localized action of cleaning beam 366. Furthermore, the fact that cleaning and measurement are interleaved in time allows a lower cleaning beam power to be used than is the case where cleaning and measurement are separated in space and time (i.e., where cleaning intervals are much greater). This lower cleaning beam power also serves to reduce the possibility of damage to the sample. The risk of damage can be further reduced by performing the cleaning operation on non-functional regions of test sample 310 (e.g., regions such as scribe lines that will not be part of the functional portion(s) of the final devices to be made from test sample 310).

To minimize the effect of the interleaved cleaning process on the beam characteristic measurements being taken by metrology system 300, cleaning beam emitter 362 shown in FIG. 3b can provide cleaning beam 366 as a pulsed beam. According to an embodiment of the present invention, cleaning beam source 363 could comprise a pulsed laser. For example, contaminant layer 313 could comprise a 5 angstrom thick layer of water and organic materials (which is similar to contamination layers often formed on modern thin film layers during production). A number of pulses or even a single pulse from a 5–100 μJoule laser having a 1–100 ns pulse duration could then heat the desired portion of contaminant layer 313 to between roughly 300° C. to 1000° C., which is a temperature range sufficient to vaporize that portion of contaminant layer 313.

According to another embodiment of the invention, cleaning beam source 363 could comprise a Q-switched laser delivering a relatively, high peak power, such as a frequency-doubled or tripled YAG (yttrium aluminum garnet) laser operating at wavelengths of 532 nm or 355 nm, respectively. According to another embodiment of the invention, other types of pulsed lasers operating at different wavelengths might be used including pulsed diode or alexandrite lasers.

According to another embodiment of the invention, a continuous laser, such as an argon-ion laser, could be externally modulated (such as with an acousto-optic or electro-optic modulator) to produce pulses. According to another embodiment of the invention, cleaning beam source 363 could comprise a flashlamp coupled to focusing optics to direct the high intensity light to the desired area on contaminant layer 313. According to other embodiments of the invention, cleaning beam emitter 362 can comprise a pulsed microwave source, a pulsed gas jet source, a pulsed acoustic source, a pulsed dry ice jet, or a pulsed ion beam source.

To provide the desired amount of initial cleaning, cleaning subsystem 360 can apply cleaning beam 366 to analysis location 314 until a predefined number of pulses have been applied to the region. Note that the duration and/or period of the cleaning pulses in cleaning beam 366 during this initial cleaning process do not necessarily have to be the same as the duration and/or period of the cleaning pulses used for the interleaved cleaning operation (i.e., the cleaning operation performed concurrently with the measurement operation). The cleaning pulses of cleaning beam 366 form an opening 315 in contaminant layer 313, as shown in FIG. 3d, through which the actual measurement operation can them be performed.

Figure 3D:
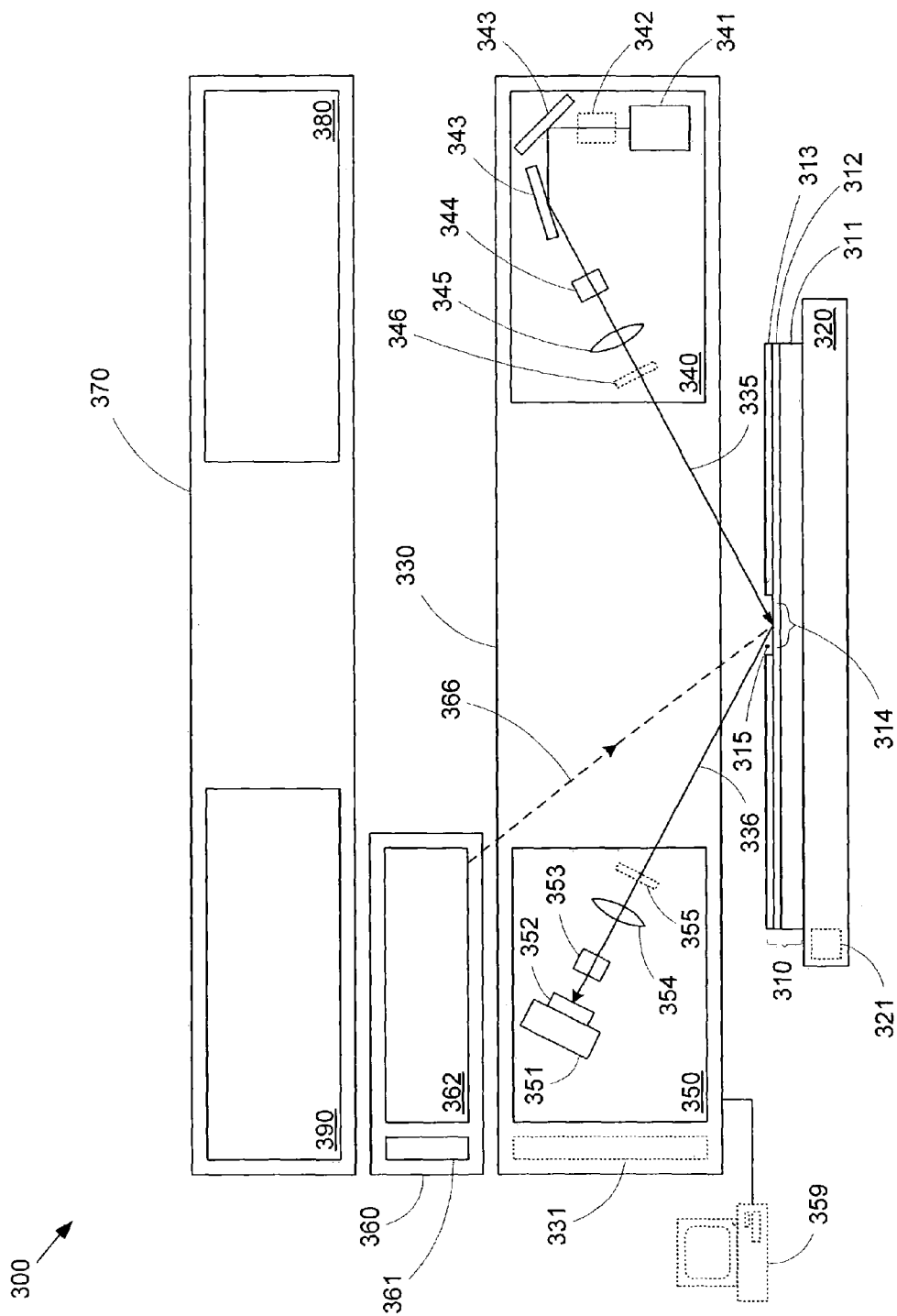

For explanatory purposes, measurement subsystem 330 is shown in FIG. 3d as comprising a measurement emitter 340 and a measurement receiver 350, and an optional computer 359. Measurement emitter includes a measurement beam source 341, an optional acousto-optical modulator 342, directional optics 343, a polarizer 344, a focusing lens 345 and a rotating waveplate 346. Measurement receiver 350 includes a detector circuit 351, an interference filter 352, a polarizer 353, a focusing lens 354, and a rotating waveplate 355. Therefore, measurement subsystem 330 as shown in FIG. 3d includes components for performing single wavelength ellipsometry (SWE), such as described in co-owned, co-pending U.S. patent application Ser. No. 09/298,007, herein incorporated by reference. Note, however, that as mentioned above, analysis subsystem 330 can comprise any type of analytical assembly, including spectroscopic ellipsometry (SE, such as described in co-owned U.S. Pat. No. 5,608,526, herein incorporated by reference), reflectometry (optical or x-ray, such as described in co-owned U.S. Pat. No. 5,747,813, herein incorporated by reference, or GXR, such as described in co-owned, co-pending U.S. Patent Application, herein incorporated by reference), non-contact electrical analysis (such as described in co-owned U.S. Pat. No. 5,485,091, herein incorporated by reference), XRF, EMP, SEM inspection/review, or contact-based electrical analysis (e.g., spreading resistance analysis), among others.

To perform an SWE measurement process, measurement beam source 341 generates a measurement beam 335. According to an embodiment of the invention, measurement beam source 341 can comprise a helium-neon (HeNe) laser with a wavelength of 633 nm. Optional acousto-optical modulator 342 can then be used to pulse measurement beam 335 if desired. Directional optics 343 direct measurement beam 335 through polarizer 344 and then through focusing lens 345. Passing through rotating waveplate 346, measurement beam 335 has its polarization continuously modulated from circular to linear and back again and directed onto the portion of thin film layer 312 exposed through opening 315 in contaminant layer 313 (i.e., analysis location 314). In response to measurement beam 335, an output beam 336 is generated from (in this case reflected by) analysis location 314. Note that depending on the specific measurement process being used, output beam 336 can comprise a single beam (e.g., if the measurement process comprises ellipsometry) or multiple beams (e.g., if the measurement process comprises XRF). Output beam 336 passes through rotating waveplate 355, focusing lens 354, polarizer 353, and interference filter 352 before striking detector circuit 351 (typically a photodiode circuit). Detector circuit 351 measures the resulting intensity profile as a function of time to allow calculation of the desired thin film characteristics—for example, by optional computer 359.

Figure 4:
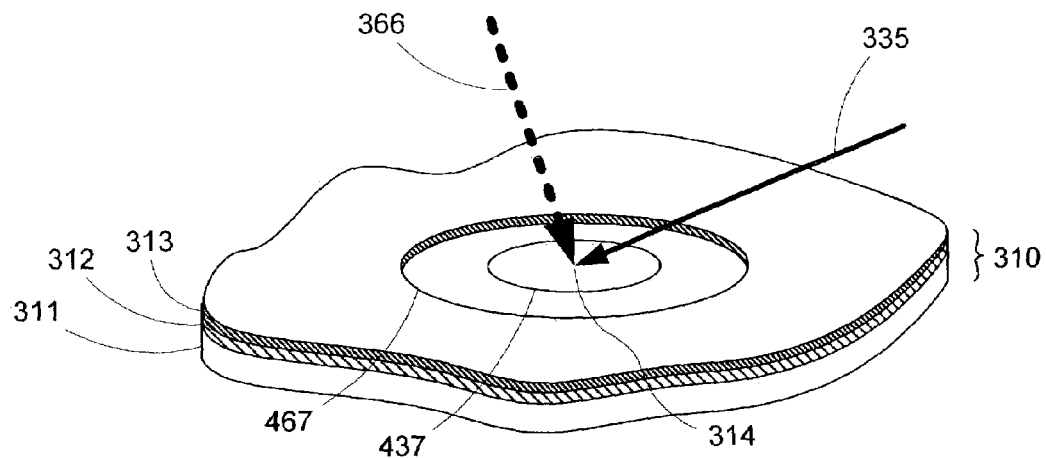
FIG. 4 is a beam diagram showing localized cleaning and measurement in accordance with an embodiment of the invention.

To ensure that accurate measurements are taken by measurement subsystem 330, measurement beam 335 must have clear access to analysis location 314. Accordingly, the specific amount of contaminant layer 313 to be removed by cleaning beam 366 depends on the beam characteristics of measurement beam 335 (and the measurement characteristics of measurement subsystem 330). Modern thin film analysis tools generally require an analysis area of at least 20 μm×20 μm. Accordingly, at least a 20 μm×20 μm portion of contaminant layer 313 would need to be removed for such systems. However, to ensure that the entire analysis area is uniformly cleaned, a larger portion of contaminant layer 313 could be removed. FIG. 4 shows a detail view of the portion of test sample 310 around analysis location 314, showing relative sizes of a cleaning beam spot 467 (through contaminant layer 313) produced by cleaning beam 366 and a measurement beam spot 437 (on thin film layer 312) produced by measurement beam 335, according to an embodiment of the invention. By focusing measurement beam 335 down to a smaller spot size (at analysis location 314) than the spot size of cleaning beam 366, greater tolerance for x-y alignment between alignment subsystem 330 and cleaning subsystem 360 (shown in FIG. 3b) is provided.

Figure 5:
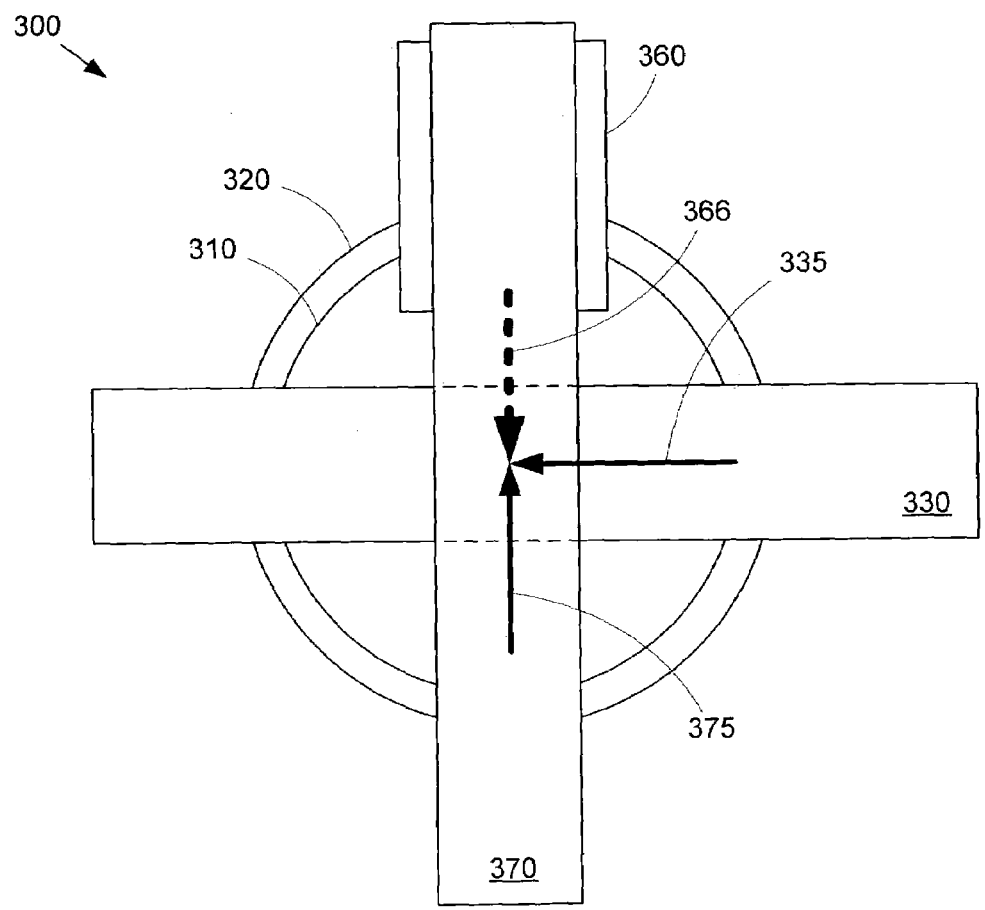
FIG. 5 is a plan view of the metrology system of FIGS. 3a–3c in accordance with an embodiment of the invention.

Note that while FIGS. 3a–3d show measurement subsystem 330, cleaning subsystem 360, and focusing subsystem 370 in a "stacked" configuration for explanatory purposes, the subsystems can take any desired arrangement. For example, FIG. 5 shows a plan view of metrology system 300 in accordance with an embodiment of the invention. While cleaning subsystem 360 remains aligned with focusing subsystem 370, measurement subsystem 330 is oriented perpendicular to focusing subsystem 370, such that the plan view directional component (i.e., parallel to the surface of test sample 310) of measurement beam 335 is perpendicular to the plan view directional components of cleaning beam 366 and alignment beam 375 (note that other non-parallel arrangements could also be implemented). This perpendicular arrangement can allow measurement subsystem 330 and focusing subsystem 340 to be more efficiently packed into metrology system 330.

The concurrent application of cleaning beam 366 to analysis location 314 during the measurement process clears away any regrowth of contaminant layer 313 in opening 315 that would otherwise compromise the accuracy of the measurement data. However, depending on the characteristics of cleaning beam 366, the individual cleaning pulses of the beam may or may not introduce some inaccuracy into the measurements taken by measurement subsystem 330 by disturbing the test sample away from an analysis baseline condition. For example, if cleaning beam 366 comprises laser pulses for vaporizing AMC on the surface of test sample 310, localized heating produced by those laser pulses may affect measurement accuracy. Also, the cleaning beam may cause an excess of charge carriers in and around analysis location 314 that can affect the metrology operation and produce erroneous results. Other cleaning effects may induce similar disturbances. According to an embodiment of the invention, because the recovery period from disturbances caused by such "cleaning effects" is typically much shorter than the time required for significant AMC regrowth, cleaning effects can simply be ignored; i.e., any measurement inaccuracy due to the cleaning beam will simply be accepted.

According to other embodiments of the invention, the cleaning effects can be compensated for in various ways, such as properly setting cleaning pulse timing, adjusting the measurement sampling characteristics, or selectively processing the raw data measurements. According to an embodiment of the invention, implementation of any of these compensation techniques can be simplified by setting the cleaning pulse rate (i.e., the number of cleaning pulses per unit time) of cleaning beam 366 equal to a submultiple of the sampling rate of measurement system 330, in which case cleaning beam 366 would introduce a substantially constant cleaning effect at constant intervals.

FIG. 6a shows an example sampling rate graph for detector circuit 351 of measurement subsystem 330 shown in FIG. 3d. The data sampling begins at a time to, and has a sampling period Ps (i.e., the time between the start of one sampling pulse and the start of the next sampling pulse; equal to 1/sampling rate) and sample width Ws (i.e., the duration of a sampling pulse). Nine samples are shown, taken at times t0–t8 (although any number of samples can be taken). FIG. 6b shows an example cleaning pulse graph for cleaning beam 366 of cleaning subsystem 360 (shown in FIG. 3d) that could be used in conjunction with the sampling rate profile shown in FIG. 6a. Prior to time to (i.e., prior to the start of data sampling), a quantity of cleaning pulses having an intensity IN', widths Wc' and a period Pc' are applied to the test sample beginning at time t0' to perform the initial cleaning operation described with respect to FIG. 3b. Once data sampling has begun (i.e., after time T0), cleaning pulses are applied having an intensity IN, widths Wc and period Pc. Note that cleaning pulse intensity IN, width Wc, and period Pc can be different from cleaning pulse intensity IN', width Wc' and period Pc', respectively. For example, to reduce the time required for the initial cleaning operation, cleaning pulse width Wc' can be set larger than cleaning pulse width Wc and/or period Pc' can be set shorter than period Pc.

FIG. 6c shows a possible temperature profile for test sample 310 shown in FIG. 3d when subjected to cleaning beam 366 having the cleaning pulse profile shown in FIG. 6b. Each cleaning pulse shown results in a corresponding temperature spike—i.e., cleaning pulses at times tc1, tc2, and tc3 shown in FIG. 6b, produce corresponding temperature spikes at the same times in FIG. 6c. As indicated, the local temperature of the test sample rises from a steady-state temperature Tss to an elevated temperature Tel. Because the analysis location is generally a small portion of a much larger test sample, any heating from a cleaning pulse is rapidly dissipated, hence the narrow widths of the temperature spikes shown in FIG. 3c. For example, in a silicon wafer, the temperature spike from a 60 ns cleaning pulse from a 532 nm laser will have a width on the order of 1 µs.

According to an embodiment of the invention, by timing the cleaning pulses to fall between data samples, the temperature disturbances caused by the cleaning pulses have time to dissipate and therefore not affect the actual measurements. By setting the cleaning pulses to occur immediately after the completion of a data sample, the allowable recovery period (cooling time) for that cleaning pulse can be maximized. For example, time tc1 of FIG. 6b could be set equal to time t2 of FIG. 6a added to sample width Ws. Similarly, time tc2 could be set equal to time t5 added to sample width Ws and time tc3 could be set equal to time t8 added to sample width Ws.

Note that even if some portion of cleaning-induced temperature effects "bleeds" into some of the data samples, by averaging multiple samples to obtain final measurements, such transient heating effects will be "smoothed out". This smoothing effect can be enhanced by increasing the sampling rate of the detection circuit (e.g., photodiode detection circuit 351 shown in FIG. 3d). However, the higher the sampling rate of the detector, the more susceptible the detector becomes to high frequency noise.

To avoid the problem of high frequency noise, a metrology system in accordance with another embodiment of the invention includes a low-bandwidth measurement receiver coupled with a measurement emitter that includes a modulator for the measurement beam (e.g., acousto-optical modulator 342 shown in FIG. 3d). Then, a high-frequency modulated measurement beam can be used to provide the desired high sampling rate, while the low bandwidth detector minimizes the problem of high-frequency noise. The modulator blocks the measurement beam during the cleaning pulse and any subsequent cooling period so that no information from the sample is received during cleaning (and cooling) operations. The modulator can also block the measurement beam between sampling pulses to avoid introducing artifacts at the cleaning laser pulse rate. Blocking the measurement laser between each sampling pulse would introduce a known, fixed artifact at the sampling rate that can be accounted for in downstream processing, thereby effectively making each inter-sampling interval identical, whether or not a cleaning pulse occurs.

Figure 7:
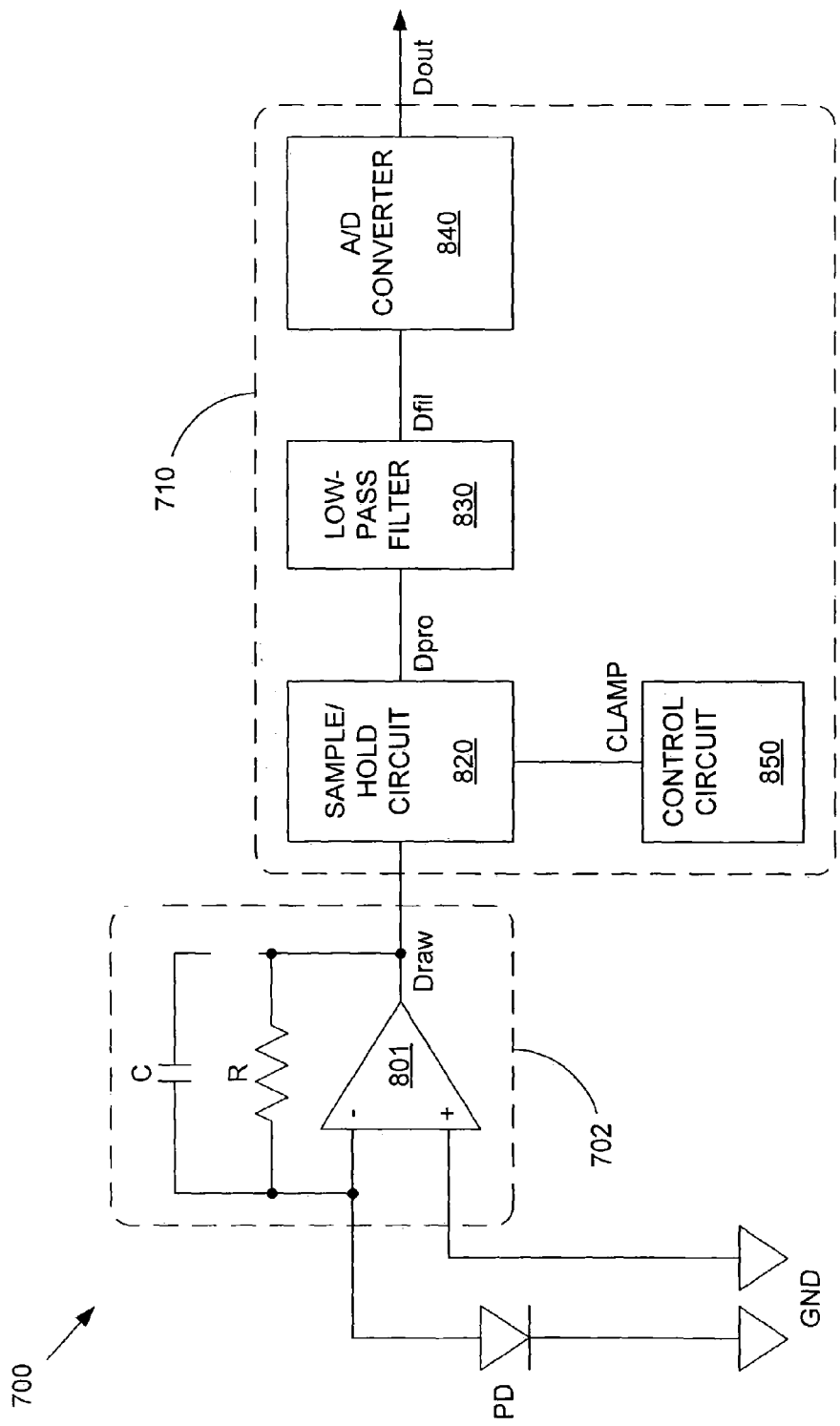
FIG. 7 is a schematic diagram of a clamping circuit according to an embodiment of the invention.

According to another embodiment of the invention, the detection circuit includes a clamp circuit to blank out any information received from the sample during cleaning pulses (and any subsequent recovery-period). FIG. 7 shows a photodiode detector circuit 700 in accordance with an embodiment of the invention. Photodiode detector circuit 700 includes a photodiode PD, an amplifier circuit 702, and a clamp circuit 710. Amplifier circuit 702 comprises an op-amp 701, a resistor R, and a capacitor C. Photodiode PD is connected to the negative input terminal of op-amp 701, and resistor R and capacitor C are connected in parallel across the negative and output terminals of op-amp 701 to control the time constant (and therefore the bandwidth) of the amplifier circuit. Clamp circuit 710 includes a sample/hold circuit 720, a low-pass filter 730, an analog-to-digital (A/D) converter 740, and a control circuit 750. Note that the bandwidth of amplifier circuit 702 should be greater than the sampling rate of A/D converter 740 to ensure that raw data Draw always provides a valid data signal to sample/hold circuit 720.

Sample/hold circuit 720 is coupled to receive raw data Draw from op-amp 701 and a control signal CLAMP from control circuit 750. During non-cleaning periods of operation, sample/hold circuit passes raw data Draw as processed data Dpro to low-pass filter 730, which in turn filters out any high frequency noise and passes filtered data Dfil to A/D converter 740, which samples filtered data Dfil to generate final output data Dout. However, during cleaning operations (and any subsequent recovery periods), control circuit 750 asserts control signal CLAMP, which places sample/hold circuit 720 into hold mode. This causes sample/hold circuit 720 to set processed data Dpro to the level of raw sample data Draw just prior to the start of the cleaning operation and hold processed data Dpro at that level until after the cleaning and recovery period has passed.

According to another embodiment of the invention, data processing software in optional-computer 359 shown in FIG. 3d can be used to delete data samples taken during cleaning operations and any subsequent recovery periods. This data deletion will generally not be problematic since the data is typically highly oversampled. According to another embodiment of the invention, the data processing software could replace the deleted data samples with data equal to the last data sample taken before the start of the cleaning operation.

According to another embodiment of the invention, measurement subsystem 330 shown in FIG. 3b comprises a spectroscopic ellipsometry (SE) measurement system, in which rotating waveplates 346 and 355 are not present, and polarizer 353 comprises a rotating analyzer. In an SE measurement system, the intensity of output beam 336 is low, so that any measurements of this beam must be integrated over many milliseconds by detector circuit 351 before being read out. At least eight such integrations ("readout cycles") must be performed during one rotation of polarizer 353. According to an embodiment of the invention, the cleaning pulses in cleaning beam 366 can be synchronized with the readout timing of detector circuit 351 so that there are a constant integer number of cleaning pulses per readout cycle. The transient perturbations caused by the cleaning pulses are then accepted and taken to be constant. According to another embodiment of the invention, measurement beam source 341 can be a broadband flashlamp or pulsed plasma source that fires at a predetermined rate, and the cleaning pulses of cleaning beam 366 are timed to fall between firings such that any disturbances such as temperature spikes are allowed to dissipate before the next measurement is taken.

The various embodiments of the structures and methods of this invention that are described above are illustrative only of the principles of this invention and are not intended to limit the scope of the invention to the particular embodiments described. Thus, the invention is limited only by the following claims and their equivalents.

The invention claimed is:

1. A method for analyzing a test sample, the method comprising:
    performing a metrology operation at an analysis location on the test sample, the metrology operation including directing a measurement beam at the analysis location;
    directing a first cleaning beam at the analysis location during the metrology operation, the cleaning beam being configured to remove contaminant material at the analysis location; and
    adjusting a position of the test sample to simultaneously focus the first cleaning beam and the measurement beam on the analysis location.

2. The method of claim 1, wherein the first cleaning beam comprises a pulsed cleaning beam.

3. A method for analyzing a test sample, the method comprising:
    performing a metrology operation using a measurement beam at an analysis location on the test sample;
    directing a first cleaning beam at the analysis location during the metrology operation, the first cleaning beam being configured to remove contaminant material at the analysis location; and
    directing a second cleaning beam at a first portion of a contaminant layer overlying the analysis location,
    wherein directing the second cleaning beam at the first portion of the contaminant layer is performed prior to performing the metrology operation at the first analysis location.

4. The method of claim 3, wherein the first cleaning beam comprises a series of first cleaning pulses having a first period, each of the first cleaning pulses having a first width and a first intensity, and
    wherein the second cleaning beam comprises a series of second cleaning pulses having a second period, each of the second cleaning pulses having a second width and a second intensity, wherein at least one of the second period, the second width, and the second intensity is different from the first period, the first width, and the first intensity, respectively.

5. The method of claim 3, wherein the first cleaning beam comprises a series of first cleaning pulses, and wherein analyzing the test sample further comprises sampling an output beam generated from the analysis location in response to the measurement beam using a series of sampling pulses, each of the first cleaning pulses occurring between sampling pulses.

6. The method of claim 5, wherein each of the first cleaning pulses occurs immediately after one of the sampling pulses.

7. A method for analyzing a test sample, the method comprising:
    performing a metrology operation at an analysis location on the test sample, the metrology operation including directing a measurement beam at the analysis location;
    directing a first cleaning beam at the analysis location during the metrology operation, the first cleaning beam being configured to remove contaminant material at the analysis location, wherein the first cleaning beam comprises a series of first cleaning pulses ; and
    sampling an output beam generated from the analysis location in response to the measurement beam at a sampling rate, and wherein the first cleaning beam comprises a cleaning pulse rate, the cleaning pulse rate being equal to a submultiple of the sampling rate.

8. A method for analyzing a test sample, the method comprising:

performing a metrology operation at an analysis location on the test sample, the metrology operation including directing a measurement beam at the analysis location;

directing a first cleaning beam at the analysis location during the metrology operation, the first cleaning beam, which comprises a series of first cleaning pulses, being configured to remove contaminant material at the analysis location; and sampling an output beam generated from the analysis location in response to the measurement beam using a series of sampling pulses at a sampling rate, wherein directing the measurement beam at the analysis location comprises:

modulating the measurement beam into a series of measurement pulses having a measurement pulse rate, the measurement pulse rate being equal to the sampling rate; and blocking the measurement beam during each of the first cleaning pulses.

9. The method of claim 8, wherein each of the first cleaning pulses heats the analysis location above a baseline temperature, the analysis location returning to the baseline temperature after a cooldown period after each first cleaning pulse, wherein directing the measurement beam at the first analysis location further comprises blocking the measurement beam during the cooldown period after each first cleaning pulse.

10. The method of claim 9, wherein directing the measurement beam at the analysis location further comprises blocking the measurement beam between sampling pulses.

11. A method for analyzing a test sample, the method comprising:

performing a metrology operation using a measurement beam at an analysis location on the test sample;

directing a first cleaning beam at the analysis location during the metrology operation, wherein the first cleaning beam comprises a series of first cleaning pulses, the first cleaning pulses being configured to remove contaminant material at the analysis location;

gathering data samples of beam characteristics for an output beam generated from the analysis location in response to the measurement beam; and clamping the data samples at a first level during each of the first cleaning pulses, the first level comprising the beam characteristics for the output beam just prior to each of the first cleaning pulses.

12. The method of claim 11, wherein each of the first cleaning pulses disturbs the analysis location from a baseline condition, the analysis location returning to the baseline condition after a recovery period after each first cleaning pulse, wherein analyzing the test sample further comprises clamping the data samples at the first level during the recovery period after each first cleaning pulse.

13. A method for analyzing a test sample, the method comprising:

performing a metrology operation at an analysis location on the test sample, the metrology operation including directing a measurement beam at the analysis location;

directing a first cleaning beam at the analysis location during the metrology operation, the first cleaning beam being configured to remove contaminant material at the analysis location, wherein the first cleaning beam comprises a series of first cleaning pulses;

gathering data samples from an output beam generated from the analysis location in response to the measurement beam; and deleting data samples taken during each of the first cleaning pulses.

14. The method of claim 13, wherein each of the first cleaning pulses disturbs the analysis location from a baseline condition, the analysis location returning to the baseline condition after a recovery period after each first cleaning pulse, wherein analyzing the test sample further comprises deleting data samples taken during the recovery period after each first cleaning pulse.

15. A method for analyzing a test sample, the method comprising:

performing a metrology operation at an analysis location on the test sample, the metrology operation including directing a measurement beam at the analysis location;

directing a first cleaning beam at the analysis location during the metrology operation, the first cleaning beam being configured to remove contaminant material at the analysis location, wherein the first cleaning beam comprises a series of first cleaning pulses;

gathering data samples from an output beam generated from the analysis location in response to the measurement beam; and replacing data samples taken during each first cleaning pulse with a first data sample taken just before the each first cleaning pulse.

16. The method of claim 15, wherein each of the first cleaning pulses disturbs the analysis location from a baseline condition, the analysis location returning to the baseline condition after a recovery period after each first cleaning pulse, wherein analyzing the test sample further comprises replacing data samples taken during the recovery period after each first cleaning pulse with the first data sample.

17. A metrology system for analyzing a test sample, the metrology system comprising:

an analysis subsystem for performing an analysis operation at an analysis location on a first surface of the test sample to analyze the test sample, wherein the analysis subsystem comprises a measurement emitter for directing a measurement beam at the analysis location;

a cleaning subsystem for directing a cleaning beam at the analysis location during the analysis operation to remove contaminant material from the analysis location; and a focusing subsystem for positioning the analysis subsystem and the cleaning subsystem so that the measurement beam and the pulsed cleaning beam are simultaneously focused on the analysis location.

18. The metrology system of claim 17, wherein the focusing subsystem directs a focusing beam at the test sample to determine a position of the test sample, the focusing beam having a first directional component parallel to the first surface, the measurement beam having a second directional component parallel to the first surface, the first directional component being nonparallel with the second directional component.

19. The metrology system of claim 17, wherein the focusing subsystem comprises:

a focusing emitter for directing an alignment beam at the test sample to generate a reflected beam; and a focusing receiver for measuring positional characteristics of the reflected beam.

20. The metrology system of claim 19, wherein the focusing emitter comprises a white-light lamp for generating the alignment beam, a first near-infrared (NIR) filter positioned in-line with the alignment beam from the white-light lamp, a first set of directional optics for directing the alignment beam through a first set of focusing optics, the first set of focusing optics focusing the alignment beam onto the test sample, and wherein the focusing receiver comprises a second set of directional optics for focusing the reflected beam onto a position-sensitive detector through a second NIR filter via a second set of directional optics.

21. The metrology system of claim 19, wherein the cleaning subsystem comprises a cleaning beam source for generating the pulsed cleaning beam, first set of directional optics for directing the pulsed cleaning beam at a dichroic mirror, the dichroic mirror being configured to reflect the pulsed cleaning beam through a first set of focusing optics onto the analysis location, wherein the focusing emitter comprises a white-light lamp for generating the alignment beam, a first NIR filter positioned in-line with the alignment beam from the white-light lamp, a second set of directional optics for directing the alignment beam through a second set of focusing optics, the second set of focusing optics focusing the alignment beam onto the test sample, and wherein the focusing receiver comprises a position-sensitive detector, a third set of directional optics, and a second NIR filter, the first set of focusing optics focusing the reflected beam through the dichroic mirror and into the third set of directional optics, the third set of directional optics directing the reflected beam through the second NIR filter onto the position-sensitive detector.

22. The metrology system of claim 17, wherein the analysis subsystem comprises one of a single-wavelength ellipsometer (SWE), a spectroscopic ellipsometer (SE), a reflectometer, a non-contact electrical measurement system, a grazing x-ray reflectometry system (GXR), an x-ray fluorescence (XRF) system, an electron microprobe analysis (EMP) system, a contact-based electrical measurement system, and a scanning electron microscope inspection/review system.

23. The metrology system of claim 17, wherein the analysis subsystem further comprises:

a measurement receiver for taking measurement samples of beam characteristics for an output beam generated from the analysis location in response to the measurement beam.

24. A metrology system for analyzing a test sample, the metrology system comprising:

an analysis subsystem for performing an analysis operation at an analysis location on a first surface of the test sample to analyze the test sample, wherein the analysis subsystem comprises:

a measurement emitter for generating a measurement beam, wherein the measurement emitter comprises an acousto-optical modulator for modulating the measurement beam; and a measurement receiver for taking measurement samples of beam characteristics for an output beam generated from the analysis location in response to the measurement beam; and a cleaning subsystem for directing a cleaning beam at the analysis location during the analysis operation to remove contaminant material from the analysis location.

25. The metrology system of claim 24, wherein the cleaning beam comprises a series of cleaning pulses, and wherein the measurement receiver comprises a clamp circuit for clamping the measurement samples taken during each cleaning pulse at a first level, the first level comprising beam characteristics from a reference measurement sample taken just before the each cleaning pulse.

26. The metrology system of claim 25, wherein each cleaning pulse disturbs the analysis location from a baseline condition for a first duration after the each cleaning pulse, the clamp circuit further clamping the measurement samples taken during the first duration after each cleaning pulse at the first level.

27. The metrology system of claim 25, wherein the measurement receiver further comprises:

a detector for generating data signals in response to the output beam;

an amplifier circuit for amplifying the data signals into raw measurement data;

a sample/hold circuit configured to pass the raw measurement data as processed data;

a low-pass filter coupled to filter high frequency noise from the processed data to generate filtered data;

an analog-to-digital (A/D) converter for sampling the filtered data to generate a set of output data; and a control circuit for providing a clamp signal to the sample/hold circuit, the clamp signal causing the sample/hold circuit to maintain the level of the processed data constant until the clamp signal is deasserted, the control circuit asserting the clamp signal during each cleaning pulse.

28. The metrology system of claim 27, wherein each cleaning pulse disturbs the analysis location from a baseline condition for a first duration after the each cleaning pulse, the control circuit further asserting the clamp signal during the first duration after each cleaning pulse.

29. The metrology system of claim 24, wherein the analysis subsystem is configured to collect data samples of beam characteristics for an output beam generated from the analysis location in response to the measurement beam, and wherein the cleaning beam comprises a series of cleaning pulses, the metrology system further comprising a computer for discarding data samples taken during each cleaning pulse.

30. The metrology system of claim 29, wherein each cleaning pulse disturbs the analysis location from a baseline condition for a first duration after the each cleaning pulse, the computer further discarding data samples taken during the first duration after each cleaning pulse.

31. A metrology system for analyzing a test sample, the metrology system comprising:

an analysis subsystem for directing a measurement beam at an analysis location on a first surface of the test sample to analyze the test sample, wherein the analysis subsystem is configured to collect data samples of beam characteristics for an output beam generated from the analysis location in response to the measurement beam;

a cleaning subsystem for directing a cleaning beam at the analysis location during the analysis operation to remove contaminant material from the analysis location, wherein the cleaning beam comprises a series of cleaning pulses ; and a computer for replacing data samples taken during each cleaning pulse with a data sample taken just before the each cleaning pulse.

32. The metrology system of claim 31, wherein each cleaning pulse heats the analysis location above a baseline temperature for a first duration after the each cleaning pulse, the computer further replacing data samples taken during the first duration after each cleaning pulse with the data sample taken just before the each cleaning pulse.

33. A metrology system for analyzing a test sample, the metrology system comprising:
- means for performing a metrology operation at a analysis location on a first surface of the test sample, wherein the means for performing the metrology operation comprises a measurement emitter for directing a measurement beam at the analysis location;
- means for cleaning the analysis location comprising means for directing a cleaning beam at the analysis location during the metrology operation to remove contaminant material from the analysis location; and
- means for positioning the analysis subsystem and the cleaning subsystem so that the measurement beam and the cleaning beam are simultaneously focused on the analysis location.

34. The metrology system of claim 33, wherein the metrology operation comprises one of an ellipsometry analysis, a reflectometry analysis, an x-ray fluorescence analysis, an electron microprobe analysis, a contact-based electrical analysis, and a scanning electron microscope inspection/review.

35. The metrology system of claim 33, wherein the means for performing the metrology operation comprises:
- means for directing a measurement beam at the analysis location; and
- means for modulating the measurement beam.

36. The metrology system of claim 33, wherein the cleaning beam comprises a series of cleaning pulses, and wherein the means for performing the metrology operation comprises:
- means for directing a measurement beam at the analysis location;
- means for taking measurement samples of beam characteristics for an output beam generated from the analysis location in response to the measurement beam; and
- means for maintaining the measurement samples taken during each cleaning pulse at a first level, the first level comprising beam characteristics from a reference measurement sample taken just before the each cleaning pulse.

37. A metrology system for analyzing a test sample, the metrology system comprising:
- means for performing a metrology operation at a analysis location on a first surface of the test sample; and
- means for directing a cleaning beam including a series of cleaning pulses at the analysis location during the metrology operation to remove contaminant material from the analysis location, wherein the means for performing includes:
- means for directing a measurement beam at the analysis location;
- means for taking measurement samples of beam characteristics for an output beam generated from the analysis location in response to the measurement beam; and
- means for maintaining the measurement samples taken during each cleaning pulse at a first level, the first level comprising beam characteristics from a reference measurement sample taken just before the each cleaning pulse; and wherein each cleaning pulse disturbs the analysis location from a baseline condition for a first duration after the each cleaning pulse, the means for maintaining the measurement samples further maintaining the measurement samples taken during the first duration after each cleaning pulse at the first level.

38. A metrology system for analyzing a test sample, the metrology system comprising:
- an analysis subsystem for directing a measurement beam at an analysis location on a surface of the test sample to analyze the test sample, wherein the analysis subsystem is configured to collect data samples of beam characteristics for an output beam generated from the analysis location in response to the measurement beam; and
- a cleaning subsystem for directing a cleaning beam at the analysis location to remove contaminant material from the analysis location,
- wherein the analysis subsystem and the cleaning subsystem share a common optical path.

39. The metrology system of claim 38, wherein the analysis subsystem includes a position sensitive detector, and wherein the cleaning subsystem includes a lens for focusing the cleaning beam at the analysis location and for focusing the output beam onto the position sensitive detector.

40. The metrology system of claim 39, wherein the cleaning subsystem further includes a dichroic mirror that reflects the cleaning beam and transmits the output beam, thereby placing the cleaning beam and the output beam in alignment.

* * * * *